United States Patent [19]
Kocher

[11] Patent Number: 6,043,342
[45] Date of Patent: Mar. 28, 2000

[54] PDZK1 PROTEIN CONTAINING PDZ INTERACTION DOMAINS

[75] Inventor: Olivier N. Kocher, Wayland, Mass.

[73] Assignee: Beth Israel Deaconess Medical Center, Boston, Mass.

[21] Appl. No.: 08/997,445

[22] Filed: Dec. 23, 1997

Related U.S. Application Data
[60] Provisional application No. 60/065,276, Nov. 10, 1997.

[51] Int. Cl.[7] .............................. C07K 1/00; C12Q 1/68; G01N 33/574
[52] U.S. Cl. .............................. 530/350; 435/6; 435/7.23
[58] Field of Search .................................. 530/350; 435/6, 435/7.23

[56] References Cited

PUBLICATIONS

Yang et al. Experimental Cell Research. vol. 241, No. 1. pp. 242–252, May 1998.
Kocher et al. Laboratory Investigation. vol. 78, No. 1, pp. 117–125, 1998.
White et al. Ann. Hum. Genet. vol. 62, pp. 287–290, 1998.

*Primary Examiner*—Paula K. Hutzell
*Assistant Examiner*—Lin Sun-Hoffman
*Attorney, Agent, or Firm*—David Prashker

[57] ABSTRACT

The present invention provides a unique DNA segment and a previously unknown PDZK1 protein as a marker system indicative of cells and tissues in an abnormal cellular state and which are undergoing a progressive loss of cell regulation and control. The isolated DNA sequence encodes the PDZK1 protein; and the expressed PDZK1 protein, particularly when present in large or excessive quantitative amounts, is a reliable and reproducible biochemical marker that an ongoing neoplastic development is occurring within cell and tissues of epithelial cell origin.

2 Claims, 8 Drawing Sheets

```
GAATTCCGGGCAGCTCCTCTTCCATCTCCAGAAATGACCTCCACCTTCAACC
CCCGAGAATGTAAACTGTCCAAGCAAGAAGGGCAAAACTATGGCTTCTTCCT
GCGAATTGAGAAGGACACCGAGGGCCACCTGGTCCGGGTGGTTGAGAAGTG
TAGCCCAGCAGAGAAGGCTGGCCTTCAAGATGGAGACAGAGTTCTTAGGAT
CAATGGTGTCTTTGTGGACAAAGAAGAACATATGCAGGTTGTGGATCTGGTCA
GAAAGAGTGGGAATTCAGTGACTTTACTAGTTCTGGATGGGGATTCCTATGAG
AAAGCAGTGAAAACACGGGTGGACTTGAAAGAGTTGGGTCAAAGTCAGAAGG
AGCAAGGTTTGAGTGATAATATACTTTCCCCTGTGATGAATGGAGGTGTGCAA
ACTTGGACCCAGCCCCGGCTCTGCTATCTCGTGAAGGAAGGAGGCAGCTAT
GGCTTCTCTCTGAAAACTGTCCAAGGTAAAAAGGGGGTGTACATGACTGATA
TTACACCTCAAGGTGTGGCTATGAGAGCTGGAGTTCTGGCTGATGATCACTT
GATTGAAGTGAATGGAGAGAATGTAGAGGATGCCAGCCATGAGAAAGTGGTT
GAAAAGGTGAAGAAGTCAGGAAGCCGTGTCATGTTCCTGCTGGTGGACAAAG
AAACTGACAAGCGTCATGTTGAGCAGAAGATACAATTCAAAAGAGAAACAGC
CAGTTTGAAACTGTTACCCCACCAGCCCCGAATTGTGGAGATGAAGAAAGGA
AGCAATGGCTATGGTTTCTATCTGAGGGCAGGCTCAGAACAGAAAGGTCAAA
TCATCAAGGACATAGATTCTGGAAGTCCAGCAGAGGAGGCTGGCTTGAAGAA
CAATGATCTGGTAGTTGCTGTCAACGGCGAGTCTGTGGAAACCCTGGATCAT
GACAGTGTGGTAGAAATGATTAGAAAGGGTGGAGATCAGACTTCACTGTTGG
TGGTAGACAAAGAGACGGACAACATGTACAGACTGGCTCATTTTTCTCCATTT
CTCTACTATCAAAGTCAAGAACTGCCCAATGGCTCTGTCAAGGAGGCTCCAG
CTCCTACTCCCACTTCTCTGGAAGTCTCAAGTCCACCAGATACTACAGAGGA
AGTAGATCATAAGCCTAAACTCTGCAGGCTGGCTAAAGGTGAAAATGGCTAT
GGCTTTCACTTAAATGCGATTCGGGGTCTGCCAGGCTCATTCATCAAAGAGG
TACAGAAGGGCGGTCCTGCTGACTTGGCTGGGCTAGAGGATGAGGATGTCA
TCATTGAAGTGAATGGGGTGAATGTGCTAGATGAACCCTATGAGAAGGTGGT
GGATAGAATCCAGAGCAGTGGGAAGAATGTCACACTTCTAGTCTGTGGAAAG
AAGGCCTATGATTATTTCCAAGCTAAGAAAATCCCTATTGTTTCCTCCCTGGC
TGATCCACTTGACACCCCTCCAGATTCTAAAGAAGGAATAGTGGTGGAGTCA
AACCATGACTCGCACATGGCAAAAGAACGGGCCCACAGTACAGCCTCACAT
TCTTCTTCCAATTCTGAAGATACAGAGATGTGATGAAAACAAGTAATAGCTTT
GGCTGTTTATTTGATAGCTGTTTCTGGGTATTTAATAGGAATCCTTTCTCAAGG
AATGAGTTGTGACCTGTTTACTGTCTCTTTAGAAGAAAAACTCCACTGGAAAC
CATTCACCATGTGTGACTGTCTTCTGTTATCATTTGTCTTACAGGCGGCTATT
GCAGACGGCTAATTTATGCTTAACTTAGGAAGAGATAAGGCAAGAGCTAGATT
TTTTTCATGTGATCTTTTCCAAGCTTCAACTTAACTTAACTACATTTCTCTGTAT
GATGATGTCTCTTACTTCTACAGGTTCCTTGAGCACCAAAGATGATTCATAAC
TCTGTATAGGTGACAGCTGCTTATAAAAGCATCTTAGCAGATAAGCCTATTAA
AATTGTGCTTTTGTAACAATGTTGTGGTTGCTAGAATAAATACCATGAACCCG
```

FIG.1

MTSTFNPRECKLSKQEGQNYGFFLRIEKDTEGHLVRVVEKCSPAEKAGLQDGD
RVLRINGVFVDKEEHMQVVDLVRKSGNSVTLLVLDGDSYEKAVKTRVDLKELG
QSQKEQGLSDNILSPVMNGGVQTWTQPRLCYLVKEGGSYGFSLKTVQGKKGV
YMTDITPQGVAMRAGVLADDHLIEVNGENVEDASHEKVVEKVKKSGSRVMFLL
VDKETDKRHVEQKIQFKRETASLKLLPHQPRIVEMKKGSNGYGFYLRAGSEQK
GQIIKDIDSGSPAEEAGLKNNDLVVAVNGESVETLDHDSVVEMIRKGGDQTSLL
VVDKETDNMYRLAHFSPFLYYQSQELPNGSVKEAPAPTPTSLEVSSPPDTTEE
VDHKPKLCRLAKGENGYGFHLNAIRGLPGSFIKEVQKGGPADLAGLEDEDVIIEV
NGVNVLDEPYEKVVDRIQSSGKNVTLLVCGKKAYDYFQAKKIPIVSSLADPLDT
PPDSKEGIVVESNHDSHMAKERAHSTASHSSSNSEDTEM

FIG. 2

```
1021 CTG GCT CAT TTT TCT CCA TTT CTC TAC TAT CAA AGT CAA GAA CTG CCC AAT GGC TCT GTC 1080
 330 L   A   H   F   S   P   F   L   Y   Y   Q   S   Q   E   L   P   N   G   S   V   349

1081 AAG GAG GCT CCA GCT CCT ACT CCC ACT TCT CTG GAA GTC TCA AGT CCA CCA GAT ACT ACA 1140
 350 K   E   A   P   A   P   T   P   T   S   L   E   V   S   S   P   P   D   T   T   369

1141 GAG GAA GTA GAT CAT AAG CCT AAA CTC TGC AGG CTG GCT AAA GGT GAA AAT GGC TAT GGC 1200
 370 E   E   V   D   H   K   P   K   L   C   R   L   A   K   G   E   N   G   Y   G   389

1201 TTT CAC TTA AAT GCG ATT CGG GGT CTG CCA GGC TCA TTC ATC AAA GAG GTA CAG AAG GGC 1260
 390 F   H   L   N   A   I   R   G   L   P   G   S   F   I   K   E   V   Q   K   G   409

1261 GGT CCT GCT GAC TTG GCT GGG CTA GAG GAT GAG GAT GTC ATC ATT GAA GTG AAT GGG GTG 1320
 410 G   P   A   D   L   A   G   L   E   D   E   D   V   I   I   E   V   N   G   V   429

1321 AAT GTG CTA GAT GAA CCC TAT GAG AAG GTG GTG GAT AGA ATC CAG AGC AGT GGG AAG AAT 1380
 430 N   V   L   D   E   P   Y   E   K   V   V   D   R   I   Q   S   S   G   K   N   449

1381 GTC ACA CTT CTA GTC TGT GGA AAG AAG GCC TAT GAT TAT TTC CAA GCT AAG AAA ATC CCT 1440
 450 V   T   L   L   V   C   G   K   K   A   Y   D   Y   F   Q   A   K   K   I   P   469

1441 ATT GTT TCC TCC CTG GCT GAT CCA CTT GAC ACC CCT CCA GAT TCT AAA GAA GGA ATA GTG 1500
 470 I   V   S   S   L   A   D   P   L   D   T   P   P   D   S   K   E   G   I   V   489

1501 GTG GAG TCA AAC CAT GAC TCG CAC ATG GCA AAA GAA CGG GCC CAC AGT ACA GCC TCA CAT 1560
 490 V   E   S   N   H   D   S   H   M   A   K   E   R   A   H   S   T   A   S   H   509

1561 TCT TCT TCC AAT TCT GAA GAT ACA GAG ATG TGATGAAAACAAGTAATAGCTTTGGCTGTTTATTTGATA 1629
 510 S   S   S   N   S   E   D   T   E   M   *                                        519

1630 GCTGTTTCTGGGTATTTAATAGGAATCCTTTCTCAAGGAATGAGTTGTGACCTGTTTACTGTCTCTTTAGAAGAAAAAC 1708
1709 TCCACTGGAAACCATTCACCATGTGTGACTGTCTTCTGTTATCATTTGTCTTACAGGCGGCTATTGCAGACGGCTAATT 1787
1788 TATGCTTAACTTAGGAAGAGATAAGGCAAGAGCTAGATTTTTTTCATGTGATCTTTTCCAAGCTTCAACTTAACTTAAC 1866
1867 TACATTTCTCTGTATGATGATGTCTCTTACTTCTACAGGTTCCTTGAGCACCAAAGATGATTCATAACTCTGTATAGGT 1945
1946 GACAGCTGCTTATAAAAGCATCTTAGCAGATAAGCCTATTAAAATTGTGCTTTTGTAACAATGTTGTGGTTGCTAGAAT 2024
2025 AAATACCATGAACCCG                                                                  2040
```

FIG. 3

PDZK1 PROTEIN CONTAINING PDZ INTERACTION DOMAINS

CROSS-REFERENCE

The subject matter as a whole comprising the present invention is evidence by Provisional Patent Application Ser. No. 60/065,276 filed Nov. 10, 1997 of record with the U.S. Patent and Trademark Office.

RESEARCH SUPPORT

The research investigations for the present invention were supported by grants from the Beth Israel Hospital Pathology Foundation, Inc., the Elsa U. Pardee Foundation, and the Nell and Nancy Fund.

FIELD OF THE INVENTION

The present invention is concerned generally with cellular mechanisms leading to the development of cancer; and is particularly directed to a marker identifying those genetic events and biochemical modifications which manifest and constitute the loss of functional cell regulation and control typically accompanying the changes of a medically normal cell initially into an abnormal cellular condition, and ultimately into a neoplastic or cancerous cell.

BACKGROUND OF THE INVENTION

Despite the passage of decades-long investigations by many different research investigators and clinical practitioners, many of the mechanisms involved in the development of cancers or neoplasms remain unknown or poorly understood at best. The accumulated knowledge to date, however, has made clear that successive and progressive genetic modifications in the cell and the attendant biochemical changes resulting therefrom play a major role in the development of tumors, particularly malignant cells and tissues. See for example: Lewin, B., *Genes V. Oncogenes: Gene Expression and Cancer*, Oxford University Press, 1994, pp. 1181–1229; Sager, R., *Science* (Washington, D.C.), 246: 1406–1412 (1989); Weinberg, R. A., *Cancer* (Phila.) 70: 1653–1658 (1992); Cotran et al., "Pathologic Basis of Disease," in *Neoplasia*, W.B. Saunders Co., 1994, pp. 241–303; Lee et al., *J. Cell Biol.* 118: 1213–1221 (1992); Lee et al., *Proc. Natl. Acad. Sci USA* 88: 2825–2829 (1991); and Chassin et al., *Cancer Res.* 54: 5217–5223 (1994).

Among the different genetic and biochemical changes associated with the progression of events constituting an ongoing neoplastic development in cells and tumors, at least two have sparked major interest and substantial enthusiasm among cancer research investigators recently. These are: The existence of PDZ domains within new proteins expressed intracellularly, and the isolation of a novel membrane associated protein, MAP17. Each of these will be summarily reviewed.

Proteins having PDZ Domains

The term "PDZ" historically corresponds to the initials of three unusual proteins, each of these proteins containing one or more specific interaction domains or regions as a functional part of their individual protein structures. These three proteins are: (a) mammalian post synaptic density protein, PSD-95 [Cho et al., *Neuron* 9: 929–942 (1992)]; (b) Drosophila disc large tumor suppressor protein [Woods, D. F. & P. J. Bryant, *Cell* 66: 451–464 (1991)]; and (c) the tight junction protein, Z0-1 [Willott et al., *Proc. Natl. Acad. Sci. USA* 90: 7834–7838 (1993)]. Since the original three PDZ domain-containing proteins were first identified and characterized, more than 50 other cytoplasmic proteins containing one or more PDZ interaction-domains have been located in areas of cell—cell contacts and synaptic junctions [Doyle et al., *Cell* 85: 1067–1076 (1996); Songyang et al., *Science* 275: 73–77 (1997)].

The PDZ domain containing proteins known to date vary greatly in range and diversity of biological/biochemical functions. Many of these PDZ domain cytoplasmic proteins are demonstrably involved in control of cell proliferation, in cell differentiation and tissue development, and in synaptic organization [Woods, D. F. & P. J. Bryant, *Cell* 6: 451–464 (1991); Cho et al., *Neuron* 9: 929–942 (1992); Li et al., *Science* 257: 1225–1230 (1992); Kim et al., *Nature* 378: 85–88 (1995); Weinman et al., *J. Clin. Invest.* 95: 2143–2149; and Poulat et al., *J. Biol. Chem.* 272: 7167–7172 (1997)].

The true function of the PDZ domains as such, however, is not yet completely understood. The PDZ domains found within the protein structure are involved in protein interactions within the cytoplasm of the cell, usually in the locale of cell—cell contacts; but such proteins are also found in the nucleus of the cell, where they play a role in tissue differentiation and development. The most recent data reported in the scientific literature suggests that proteins containing multiple PDZ domains allow the recruitment of particular molecules involved in signaling pathways within the cell and also help organize the assembly of such signaling molecules into large complexes at the membrane-cytoplasm interface [Tsunoda et al., *Nature* 388: 243–249 (1997); Yun et al., *Proc. Natl. Acad. Sci. USA* 94: 3010–3015 (1997)]. The novel expression and intracellular production of a new protein demonstrably having one or more PDZ domains is therefore presently believed to be major event associated with a progressive loss of cell regulatory control and normal cell function.

The Membrane Associated Protein, MAP17

The membrane associated protein, MAP17, was only recently identified in 1995; and within medically normal cells is significantly expressed only at the brush border of proximal tubular epithelial cells of the kidney [Kocher et al., *Clin. Cancer Res.* 1: 1209–1215 (1995)]. However, MAP17 is overexpressed in a high percentage of carcinomas derived from kidney, colon, breast, and lung; and is associated with the cell membrane either in an apical distribution pattern or in areas of cell—cell contacts [Kocher et al., *Am. J. Pathol.* 149: 493–500 (1996)]. Moreover, overexpression of MAP17 in a colon carcinoma cell line (transfected HT29 cells) produced a marked decrease (down regulation) in cell proliferation in-vitro and in tumor growth in-vivo. Consequently, it is presently believed that novel and newly expressed proteins which demonstrably interact with MAP17 are actively involved in the progression of events and changes associated with the development of neoplasms, particularly malignant tumors.

Clearly, the transformation of a medically normal cells and tissues into an abnormal condition, and then progressively into a neoplastic or cancerous state is a multistep process occurring over time. Despite the abundance of information and knowledge accumulated in the scientific literature describing and characterizing the malignant transformation process, few biochemical markers or indicators of the progressive loss of cellular regulatory controls and increasing cell dysfunction have been identified to date. For these reasons, were an accurate, reliable, and detectable biochemical marker to be isolated which is indicative of an ongoing neoplastic development and identifies a progressively-worsening abnormal state within particular cells and tissues, such a marker would be recognized as a major advance and long-sought achievement within this technical field.

SUMMARY OF THE INVENTION

The present invention has multiple aspects. A first aspect is a DNA segment encoding PDZK1 protein whose expression indicates an ongoing neoplastic development within cells and tissues of epithelial cell origin, said DNA segment comprising

- a DNA sequence of about 2.1 kilobase pairs in size;
- a DNA sequence coding for the PDZK1 protein comprised of about 519 amino acids; and
- a DNA sequence coding for four distinct PDZ domains as part of the overall structure for the expressed PDZK1 protein.

A second aspect of the invention is a PDZK1 protein whose intracellular presence indicates an ongoing neoplastic development within cells and tissues of epithelial cell origin, said PDZK1 protein comprising

- a polypeptide having a molecular weight of about 63 kD;
- a polypeptide comprised of about 519 amino acids; and
- a polypeptide having four distinct PDZ domains as part of its overall structure.

BRIEF DESCRIPTION OF THE FIGURES

The present invention may be more easily and completely understood when taken in conjunction with the accompanying drawing, in which:

FIG. 1 is a recitation of the nucleic acid sequence of PDZK1 cDNA cloned from the human kidney Matchmaker cDNA library, FIG. 2 is a recitation of the deduced amino acid sequence of PDZK1 protein;

FIG. 3 is a recitation and correlation of the PDZK1 cDNA sequence and the amino acid sequence of PDZK1 protein illustrating the four PDZ domains as boxed enclosures;

DETAILED DESCRIPTION OF THE INVENTION

Figure 4:
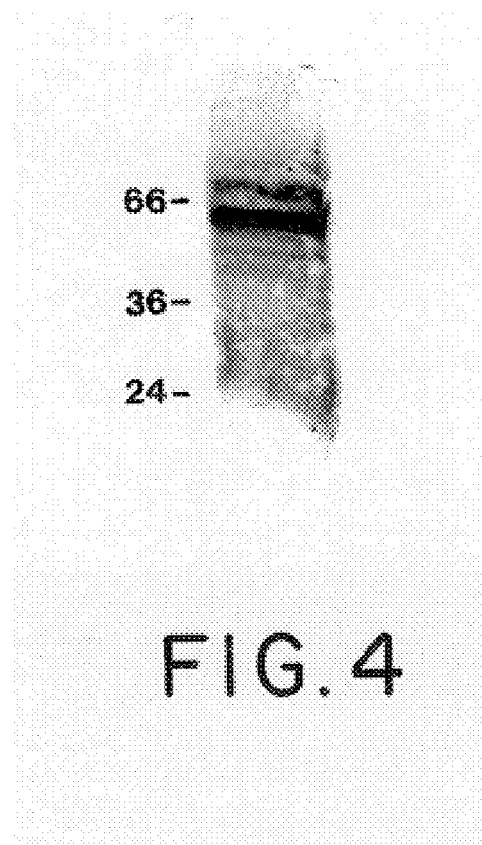
FIG. 4 is a photograph illustrating cell-free translation of PDZK1 cDNA in a reticulocyte lysate.

The present invention is a DNA and/or protein marker system for determining in-vitro whether a particular cell, tissue, or organ specimen is undergoing a progressive loss of regulatory control; is in the process of becoming increasingly abnormal; and is presently in a state of neoplastic development. The preferred marker is a unique protein of specified characteristics biochemically, and has been analyzed in detail such that its amino acid residue composition and sequencing is completely known and established.

It will be recognized and appreciated that the subject matter as a whole which is the present invention concerns itself with a very sophisticated and technically difficult medical problem; and that a general familiarity and understanding of cancer in general and malignant tumors in particular is essential in order to properly understand the present invention.

It is important also to employ some basic definitions and terms properly and precisely and to relate them to a clinical context. Many clinical and medical terms regarding cancer have a more precise meaning than is commonly appreciated. For this reason, a minimal set of definitions and terminology is presented below which will be employed in the description of the invention which follows hereinafter.

Definitions and Terminology:

Neoplasm: an abnormal mass of cells typically exhibiting uncontrolled and progressive growth. Neoplasms are broadly classified into two categories: (1) according to the cell type from which they originate; and (2) according to their biologic behavior, i.e., whether they are benign or malignant.

Cancer: a general term that by common usage has come to encompass all forms of malignant neoplasms.

Malignant: a concept referring to the tendency to become progressively worse and to result in death. With neoplasms, the term denotes the properties of invasiveness and metastasis.

Benign: mild, favorable or kindly, in oncology, the opposite of malignant. Benign neoplasms are usually well circumscribed and are often encapsulated; by definition, benign tumors do not invade locally and do not metastasize.

Metastasis: the process by which malignant cells are disseminated from the tumor of origin (the primary tumor) to form a new growth (the secondary tumor) at a distant site. It is the discontinuous extension of a malignant neoplasm.

In addition, it is also important that the user be at least familiar with the many techniques for manipulating and modifying genes and DNA fragments which have been reported and are today widespread in use and diverse in application. Merely exemplifying the many authoritative texts and published articles presently available in the literature regarding genes, DNA and RNA probes, nucleotide manipulation, and the expression of proteins from manipulated DNA are the following: *Gene Probes for Bacteria* (Macario and De Marcario, editors) Academic Press Inc., 1990; *Genetic Analysis, Principles Scope and Objectives* by John R. S. Ficham, Blackwell Science Ltd., 1994; *Recombinant DNA Methodology II* (Ray Wu, editor), Academic Press, 1995; *Molecular Cloning, A Laboratory* Manual (Maniatis, Fritsch, and Sambrook editors), Cold Spring Harbor Laboratory, 1982; *PCR (Polymerase Chain Reaction)*, (Newton and Graham, editors), Bios Scientific Publishers, 1994; and the many references individually cited within each of these publications.

I. The PDZK1 DNA and Expressed PDZK1 Protein

The present invention comprises both the DNA segment reciting the base pair sequences constituting the complete regulatory PDZK1 gene as well as the expressed PDZK1 protein which is a marker and indicator of neoplastic development in cells and tissues of epithelial cell origin. Each aspect of the invention as a whole will be individually described in detail.

The DNA of the PDZK1 Gene:

The PDZK1 DNA encoding the entire PDZK1 protein is an approximate 2.1 kilobase pair segment which presents four individual and distinct PDZ domains within the DNA sequence. A complete recitation of PDZK1 cDNA is given by FIG. 1. The individual PDZ domains within the cDNA is given by FIG. 1. The individual PDZ domains within the cDNA segment are shown by the four block enclosures placed within the cDNA and amino acid correlation presented by FIG. 3. The isolation and characterization of the PDZK1 cDNA as well as its corresponding transcribed mRNA are presented by the experiments and empirical data described hereinafter.

The PDZK1 DNA can be and is replicated as cDNA using techniques which are well recognized, procedures which have become standardized, and practices which are commonly employed today in this art. The cDNA shown by FIGS. 1 and 3 respectively encodes the whole PDZK1 protein whose expression, particularly in abundant quantities, indicates an ongoing neoplastic development within the cells where the protein is found.

The Expressed PDZK1 Protein:

The PDZK1 protein is an intracellular marker whose expression and presence, particularly in abundant quantities, indicates an ongoing neoplastic development—an abnormality within the cell—which will result eventually in a clinically apparent and identifiable carcinoma of those cells and tissues.

The PDZK1 protein is constituted as a 519 amino acid strand, the composition and amino acid residue sequence of which is recited by FIG. 2. The PDZK1 protein is about 63 kD in molecular weight; and comprises four individual and distinct PDZ domains varying in size from 54 to 80 amino acids which are shown as block enclosures within the cDNA and amino acid correlation of FIG. 3. Also, the PDZK1 protein is devoid of a SH3 binding domain; does not contain a guanylate kinase domain; but does actively interact with the membrane associated protein MAP17 (recognized as itself being overexpressed in a number of different carcinomas). The isolation, amino acid residue composition, and overall characteristics of the PDZK1 protein are described in detail by the experiments and empirical data presented hereinafter.

II. Significance of PDZK1 Protein Expression and Quantitative Presence as a Marker Overall Significance The expression and quantitative presence of the 519 amino acid residue containing PDZK1 protein has major clinical value and utility as a diagnostic marker or chemical signal of an ongoing neoplastic development in the cells and tissues of epithelial cell origin where the protein is to be found. The presence of the PDZK1 protein intracellularly, within particular cell types or tissues and/or in especially large or excessive quantitative amounts, is a reliable and reproducible indicator that the cells and tissues of interest are becoming progressively abnormal over time; and that the cells and tissues in question are in a pre-cancerous stage during which the normal regulatory and control mechanisms of the cells are becoming more and more variable, ineffective, and dysfunctional.

Among the demonstrated characteristics of the PDZK1 protein is its ability to interact intracellularly with MAP 17.

The experiments and empirical data provided hereinafter clearly demonstrate that MAP17 and PDZK1 protein interact under both in-vitro and in-vivo conditions. Such MAP17 interaction is deemed to be further evidence of a continuing and ever-worsening abnormality in the cell which is tantamount to being in a precancerous state clinically.

Distribution in Normal Cells and Tissues:

As evidenced by the empirical data presented hereinafter, PDZK1 protein is expressed in minimal or moderate quantities by selected normal cells and tissues; and only some normal cells and tissues of epithelial cell origin (rather than all types generally). Other kinds of cells (of epithelial cell origin) are not able to express and produce PDZK1 protein at all. Thus, mesenchymal cells and inflammatory cells, which are not of epithelial cell origin, but are medically and functionally normal in all clinical respects, have been shown not to express or produce PDZK1 protein. In addition, there is considerable variety in the range of normal cells and tissues of epithelial cell origin which are able to express PDZK1 protein in detectable amounts. A representative listing of such normal cells and tissues is given by Table 1 below.

TABLE 1

Normal Cells and Tissues

| Normal Tissue or Cell Type | Expression And Presence of PDZK1 Protein | Quantitative Amount of PDZK1 Protein* |
|---|---|---|
| A. Tissues (Normal) | | |
| Kidney | Yes | ++ |
| Liver | Yes | ++ |
| Pancreas | Yes | ++ |
| Small Intestine | Yes | ++ |
| Testis | Yes | + |
| Adrenal Cortex | Yes | + |
| Stomach | Yes | + |
| Heart | No | − |
| Brain | No | − |
| Placenta | No | − |
| Lung | No | − |
| Breast | No | − |
| Adrenal Medulla | No | − |
| Thyroid | No | − |
| Thymus | No | − |
| Colon | No | − |
| B. Cells (Normal) | | |
| Proximal tubular epithelial cells (kidney) | Yes | ++ |
| Renal parenchyma cells (kidney, other than proximal tubular epithelial cells) | No | − |
| Glandular epithelial cells (stomach) | Yes | + |
| Glandular epithelial cells (small bowel) | Yes | + |
| Colonic mucosa cells (large intestine) | No | − |

+ = minimal quantity
++ = moderate quantity
+++ = high quantity
++++ = excessive quantity
*Quantity above background labeling (a negative result)

The listing of Table 1 thus provides several valuable criterion and standards. These include the following: (a) Among the normal cells and tissues of epithelial cell origin which were empirically tested, only about half express PDZK1 protein in any detectable amount. (b) Even within a single organ, some cells comprising the organ tissues may express PDZK1 protein while other cell types in the organ do not. The kidney is a illustrative example of this finding, where the proximal tubular epithelial cells express the proteins while other renal parenchyma cells do not. (c) A number of organs such as the breast, colon and lung, in the medically normal state, do not express PDZK1 protein at all. (d) In those medically normal cells and tissues which consistently demonstrated expression of PDZK1 protein, only moderate or minimal quantitative amounts of protein were produced; in no instance was either a large or excessive quantity of PDZK1 protein produced by a medically normal cell or tissue.

Distribution in Neoplastic (Malignant) Cells and Tissues

The expression and production of PDZK1 protein in neoplasms of epithelial cell origin (carcinomas generally) shows a very different range and distribution among abnormal cells and tissues. A representative listing of neoplastic cells and tissues as well as their ability to express PDZK1 protein is given by Table 2 below.

TABLE 2

| Neoplastic Tissue or Cell Type | Neoplasms | |
|---|---|---|
| | Expression And Presence of PDZK1 Protein | Quantitative Amount of PDZK1 Protein* |
| Renal cell carcinoma | 75% of cases | varying: ++ to +++ |
| Infiltrating carcinomas of the breast | 55% of cases | +++ to ++++ |
| Colonic carcinomas | 25% of cases | +++ to ++++ |
| Lung carcinomas | 25% of cases | +++ to ++++ |

+ = minimal quantity
++ = moderate quantity
+++ = high quantity
++++ = excessive quantity
*Quantity above background labeling (a negative result)

The listing of Table 2 also provides valuable diagnostic criterion and standards for using the expression of PDZK1 protein as a marker of ongoing neoplastic development. These findings include: (1) In those cells and tissues which if medically normal do not express PDZK1 protein, a large number of carcinomas of such cells and tissues express and produce PDZK1 protein in either large or excessive amounts. Illustrative examples are the breast, lung and colonic carcinomas. (2) In those cells and tissues which might or might not express PDZK1 protein under medically normal conditions, a meaningful number of carcinomas of these cells and tissues express and produce PDZK1 protein in high or excessive amounts. Examples of these are the renal cell carcinomas. These are empirically based findings and supported conclusions demonstrating the value and utility of PDZK1 protein as a clinical marker.

Inferentially and indirectly, at least one additional conclusion may be drawn which has clinical impact and predictive value: In those cells and tissues which do not express PDZK1 protein under medically normal conditions, the expression and production of PDZK1 protein—even in minute amounts—will serve as a reliable indicator that the cell regulatory control mechanisms are degrading and failing. Thus, it is expected that in a number of instances involving carcinomas of the adrenal medulla, the thyroid, the thymus and the like, detectable amounts of PDZK1 protein will be expressed and produced. An empirical example supports this premise and conclusion, the colonic carcinomas which have been shown to express PDZK1 protein in an estimated 25% of cases—while the normal colonic mucosa cells have been empirically shown not to express PDZK1 protein at all.

Practical Use of the PDZK1 Protein as a Marker

Clearly, the clinical value and predictive use of PDZK1 protein expression, qualitatively and quantitatively, is a diagnostic tool requiring judgment and discretion. In general, where PDZK1 protein expression occurs in large or excessive amounts within a cell or tissue, the predictive conclusion that a neoplastic development is occurring may be made with confidence. Similarly, where the cell or tissue sample under test is a cell or tissue which does not express PDZK1 protein routinely under normal medical conditions, then even a minute quantity of PDZK1 protein production is sufficient reason to diagnose an ongoing neoplastic development in those cells or tissues of interest.

At the other test extreme, where only minimal or moderate amounts of PDZK1 protein are detected in cells or tissues which are recognized as having the capability to express PDZK1 protein under normal medical conditions; or if the cells or tissues under test are known to be variable in their ability to produce PDZK1 protein in minimal quantities under normal cell circumstances—then this test data and minimal empirical result should not and cannot be employed rationally or properly as a predictive factual basis for concluding that a neoplastic development is ongoing in that tissue sample.

III. Preferred Protocols

Some preferred detection assays and procedures are presented hereinafter for the benefit and advantage of the intended user and practitioner in the art. Several of the protocols are quite detailed in description; others are less particularized. However, all of the stated specifics—such as fluid volumes, reagent concentrations, time intervals, aliquot sizes and the like—are understood to be variables and routinely changeable in practice to meet the preferences or requirements of the user. All the procedures and protocols presented herein are deemed to be within the skill of the ordinary practitioner in the relevant field and art today, sufficient guidance and suggestions are provided within the details of the protocols to meet almost any use circumstances.

A. PDZK1 DNA Determinations

Protocol: Isolation of DNA from mammalian tissue and hybridization with a PDZK1 cDNA probe.

Preliminary Steps

1. Drop fresh tissue into liquid nitrogen and reduce it into powder using a blender.
2. Add 10 volumes of extraction buffer (10 mM Tris-Cl pH 8.0, 0.1 M EDTA, pH 8.0, 20 µg/ml pancreatic RNAse and 0.5% SDS). Incubate at 37° C. for 1 hour.
3. Add proteinase K to a final concentration of 100 µg/ml and mix gently. Incubate at 50° C. for 3 hours.
4. Cool the solution to room temperature and extract once with a solution of saturated phenol. Recover the aqueous solution by centrifugation at 5000 g for 5 minutes. Repeat the extraction twice.
5. Add 0.2 volume of 10M ammonium acetate and two volumes of ethanol. Mix gently.
6. Transfer the precipitate to a new tube, and dissolve in 1 ml of water. Measure the optical density at 260 and 280 nm.

Southern Blot Assay

1. Digest 10 µg of DNA with EcoRi for 4 hours at 37° C.
2. Run the digest on a 1% agarose gel in Tris-Borate-EDTA buffer with appropriate size markers (λ phage digested with HindIII) at 100 volts for 6 hours. Take a picture.

3. Soak the gel for 1 hour in 0.5 M NaOH-1.5 M NaCl and then for 1 hour in 1M Tris-Cl pH 8.1-1.5 M NaCl.
4. Transfer to nitrocellulose and then crosslink the DNA using ultraviolet light.
5. Hybridize the blot with a $^{32}$P-labeled PDZK1 cDNA probe in 6XSSC, 0.5 SDS, 100 µg denatured salmon sperm DNA and 50% formamide at 42° C. for 16 hours.
6. Wash the blot in 1XSSC, 0.1% SDS for 20 minutes each at 55, 60 and 65° C. 7. Wrap the blot in saran wrap and expose to film for 48 hours at −80° C.

B. Quantification of the Expression of PDZK1 Protein

The quantification of the expression of PDZK1 can be done using two techniques:
1. Quantification of the expression of PDZK1 mRNA using in situ hybridization on cultured cells or sections of tissue. The mRNA expression is evaluated using a radioactive probe which is applied to the preparation, which is subsequently coated with a photographic emulsion. After exposure, the emulsion is developed and silver grains are counted. A negative control typically contains 0–1 silver grain per cell, while a positive experiments will show 5–10 silver grains per cell.
2. Alternatively the expression of PDZK1 is estimated using our specific antibody against this protein using the immunoperoxidase technique, in which a brown signal labels the cells expressing the protein. A negative experiment does not show any brown labeling, while a positive experiment shows a brown labeling of an intensity which can be graded from 1+ to 4+.

These two techniques allow us to estimate and localize cells expressing PDZK1, in normal conditions and in cancer cells.

Protocol B1: Localization of PDZK1 mRNA by In Situ Hybridization

I. Make 4–6 µM tissue sections using a cryostat or microtome for paraffin sections.

II. Pre-hybridization

| ***** Steps 1–7 are for paraffin sections only ***** | | |
|---|---|---|
| 1. Xylene | 7 minutes | Room temp. |
| 2. Xylene | 8 minutes | Room temp. |
| 3. Xylene | 5 minutes | Room temp. |
| 4. 100% Ethanol | 1 minute | Room temp. |
| 5. 90% Ethanol | 1 minute | Room temp. |
| 6. 70% Ethanol | 1 minute | Room temp. |
| 7. 30% Ethanol | 1 minute | Room temp. |
| ***** Frozen sections start here ***** | | |
| 8. 0.2M HCl/DEPC H$_2$O | 20 minutes | Room temp. |
| 9. 10 mM Tris/1 mM EDTA DEPC H$_2$O | 5 minutes | Room temp. |
| 10. 10 mM Tris/1 mM EDTA/DEPC H$_2$O + 1 µG/mL Proteinase K (paraffins get 3 µG/ml PK) ** see note about Proteinase I | 15 minutes | 37° C. |
| 11. 0.2% Glycine/DEPC PBS | 2 minutes | Room temp. |
| 12. DEPC PBS rinse | 3 minutes | Room temp. |
| 13. 4% Paraformaldehyde/PBS | 20 minutes | Room temp. |
| 14. DEPC PBS Rinse | 5 minutes | Room temp. |
| 15. 0.1M Triethanol/1:200 Vol/Vol Acetic anhydride | 10 minutes | Room temp. |
| 16. 2× SSC Rinse | 10 minutes | Room temp. |
| 17. Incubate with $^{35}$S-labelled PD2K1 probe | overnight | 50° C. |

Note:
Step 10 - add proteinase K just before adding slides
Step 15 - add acetic anhydride just before adding slides
DEPC = diethyl pyrocarbonate;
EDTA = ethylenediamine tetracetic acid;
PBS = phosphate buffered saline;
SSC = sodium chloride/sodium citrate buffer.

III. Post-Hybridization Washes
   Volume=150 ML

| | | |
|---|---|---|
| 1. 50% formamide/2× SSC/10 MM DTT - This first solution is used for removing the coverslips from the tissue sections. Leave slides in buffer until coverslips fall off then transfer to #2. | | |
| 2. 50% formamide/2× SCC/10 mM DTT | 30 min. | 50° C. |
| 3. 50% formamide/2× SCC/10 MM DTT | 30 min. | 50° C. |
| 4. 4× SCC/10 mM Tris/1 mM EDTA | 15 min. | 37° C. |
| 5. 4× SSC/10 mM Tris/1 mM EDTA + 20 µg/mL RNAse A. | 30 min. | 37° C. |
| 6. 4× SSC/10 mM Tris/1 mM EDTA | 30 min. | 37° C. |
| 7. 50% formamide/2× SSC/10 mM DTT | 60 min. | 65° C. |
| 8. 2× SSC/DDH$_2$O | 3 min. | R.T. |
| 9. 30% Ethanol/0.3M ammonium acetate | 1 min. | R.T. |
| 10. 50% Ethanol/0.3M ammonium acetate | 1 min. | R.T. |
| 11. 70% Ethanol/0.3M ammonium acetate | 1 min. | R.T. |
| 12. 93% Ethanol/0.3M ammonium acetate | 1 min. | R.T. |

Note:
Step 5 - Add RNAse just before adding slides to buffer.
Paraffin sections - increase RNAse incubation to 60 min.
DTT = dithiothreitol IV. Interim Stage
   1. Allow slides to air dry in fume hood.
   2. Store at 4° C. with desiccant until ready to dip.

V. Developing/Staining In Situ Slides
(a) Developing
   Need 3×1000 mL beakers
   Pour 200 mls of developer into one beaker and add 200 mls ddH$_2$O
   Add 450 mls of ddH$_2$O to second beaker
   Add 400 mls of fixer to third beaker
   Put slides into slide rack and add to developer for 2 min. 30 sec.
   Dunk slides up and down in ddH$_2$O beaker to rinse
   Transfer slides in ddH$_2$O for approx. 30 minutes with one change of H$_2$O
(b) Staining

| | |
|---|---|
| 1. Take slides from H$_2$O after developing and stain in hemotoxylin for 30 seconds. Rinse well in water. | |
| 2. 95% ethanol | 30 dips |
| 3. 100% ethanol | 30 dips |
| 4. 100% ethanol | 30 dips |
| 5. 100% ethanol | 30 dips |
| 6. Xylene | 30 dips |
| 7. Xylene | 30 dips |
| 8. Xylene | 30 dips then leave in for 5 minutes |
| 9. Mount in permount | |

Addendum B1(a): Emulsion for Dipping In Situ Slides

Equipment
Emulsion (Kodak NTB-2 AR #165-4433, IBI $206.40)
2% glycerol (196 mL, ddH$_2$O+4 mL glycerol–mix well)
Pipette
14 pieces of tin foil
14 scintillation vials
Water bath set at –45° C.
Procedure
1. Warm emulsion in water bath in darkroom for about 30 minutes. Make sure water level is nearly even with top of emulsion jar or the top layer will not thaw.
2. Add 16 mls of 2% glycerol to the first scintillation vial and make a line to mark the fluid level. Mark the other 13 vials at the 16 mL mark by eyeballing against the first vial.
3. Pipette 8 mL of 2% glycerol into each vial.
4. Bring vials, 25 mL pipette, and foil into the darkroom and add 8 mL of the emulsion to each vial.
5. Cap each vial and carefully wrap each one in foil and put into storage tin. Make a note of the date of the new batch. Toss any old vials of emulsion.
6. Store vials in 4° C. in darkroom.

Addendum B1(b): Instructions for Dipping In Situ Slides

Bring small water bath set to about 37–40° C. into the darkroom and place a wrapped vial of emulsion in the bath. One vial of 16 mL will do approximately 40 slides. Let emulsion warm for minimum of 30 minutes.
Items
light-tight chamber lined with pieces of paper towel
blank slides
kim wipes
dipping chamber and stand
slides
slide boxes
foil to wrap slide boxes
Procedure
1. When emulsion is ready, unwrap the vial and carefully pour it into the dipping chamber. Let sit a few minutes.
2. Take a blank slide and lower it into the emulsion then with a slow and steady movement pull it from the emulsion. There should be lots of bubbles. Keep doing this to remove the bubbles from the emulsion. When there are no more bubbles it is ready for dipping.
3. Take an in situ slide and lower it into the emulsion. With a slow and steady motion, pull it from the emulsion. Blot the bottom of the slide on a kim wipe and then wipe the back of the slide clean. Place an end in the light-tight chamber tissue side facing the walls of the chamber. This will allow excess emulsion to drain off onto the paper towels.
4. Continue dipping slides until all are done. If you run into bubbles during the dipping process, simply take a blank slide and extract them out. Wherever there is a bubble in the emulsion on your tissue section, there will be no reaction and you will not see any results in that area when you develop the slide.
5. When all slides are done, close the light-tight chamber and let stand for 20 minutes until the emulsion can dry on the slides.
6. Put the dried slides into slide boxes containing a packet of desiccant. Wrap boxes in foil, label with dipping date, and place at 4° C.
7. The slides will be ready for developing in 2 weeks if you are using $^{35}$S probes. (If probes are 32p, it will take less time.)

Protocol B2: Detection of PDZK1 Protein Using Anti-PDZK1 Antibody

Precaution: Never allow slides to dry. High background staining results from dryness.

(a) From Cultured Cells

1. Rinse slide in Phosphate buffered saline (PBS)*.

* dip slide in beaker of PBS, aspirate, add PBS with a pipetman, aspirate again.

2. Fix cells in ice cold 4% Paraformaldehyde (must be freshly defrosted) for 20 min. Leave slide on ice during incubation.
3. Rinse slide in PBS*

* dip slide in beaker of PBS, aspirate, add PBS with a pipetman, aspirate again.

4. Permeabilize cells with 0.5% Triton X-100 in PBS for 15 min., at room temperature (RT).

(b) From Frozen Tissue Sections

5. Rinse slide in Tris Buffered Saline (TBS) pH 7.6. Soak for at least 5 minutes.
6. Block endogenous peroxidase with 2% hydrogen peroxide in methanol for 10 min., room temperature (RT). Prepare just before using.
7. Rinse in double distilled water (ddH$_2$0).
8. Rinse in TBS for 5 min., RT TWICE. Change TBS between washes. Wipe around tissue section with a kim wipe.
9. Block nonspecific binding with 5% Normal Goat Serum (NGS) (heat inactivated) in TBS for 20 min., RT.
10. Gently knock excess liquid off of slide. Wipe around tissue section with a kim wipe.
11. Add anti-PDZK1 antibody diluted 1/25 in TBS+1% NGS. Incubate for 45 min., RT in a HUMIDIFIED CHAMBER.
12. Rinse slide in TBS on an orbital shaker for 8 min., RT TWICE. Change TBS between washes. Gently knock off excess liquid off of slide. Wipe around tissue section with a kim wipe.
13. Add secondary antibody (anti-chicken IgG-biotinylated) diluted 1/200 in 50 mM Tris, pH 7.6. Incubate for 30 min., RT in a HUMIDIFIED CHAMBER.
14. Rinse slide in TBS on an orbital shaker for 8 min., RT TWICE. Change TBS between washes. Gently knock off excess liquid off of slide. Wipe around tissue section with a kim wipe.
15. Add Avidin-Biotin-Peroxidase (ABC) stain to each slide; reagent must be prepared 30 min. before use—maximum shelf life is ONE WEEK. (ABC prep: 1 drop A+1 drop BC in 5 ml 50 mM Tris pH 7.6). Incubate 30 min., RT in a HUMIDIFIED CHAMBER.
16. Rinse on an orbital shaker for 8 min., RT TWICE. Change TBS between washes. Wipe around tissue section with a kim wipe. Remove chambers from Lab-Tek slides after first wash.
17. Stain slides at room temperature with diaminobenzidine (DAB) [Research Genetics #750118] for 5 min. Be sure to wear gloves. Use ddH$_2$O to stop color development.
18. Counterstain in 1× hematoxylin (Surgipath #01562) for 10–15 sec. Wash slides in dH$_2$O (staining time is important. May need to do more than one wash to remove excess stain).
19. Dehydrate slides: a. Soak in 95% EtOH for 3 min. b,c Soak in 100% EtOH for 3 min. Replace EtOH, soak again for 3 min. Do not wet containers with water in between each step.

20. Saturate with Xylene: Soak slides in THREE xylene baths, 5 min. in each.

Notes:

Heat Inactivation in Normal Goat Serum:
heat at 56° C. for 30 min.
aliquot in 10 ml portions, store at −20° C.

Tris Buffered Saline (TBS), (5 L):
add 40.5 g NaCl and 30.28 g Tris BASE to 4.3 L ddH$_2$O
pH to 7.6
adjust volume to 5.0 L IV. Experimental and Empirical Data To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

A. Materials and Methods:

Cloning of PDZK1 Using the Yeast Two-Hybrid System

A 200 bp DNA fragment corresponding to the 64 amino acid cytoplasmic hydrophilic region of MAP17 was amplified by PCR (Polymer Chain Reaction) using specific oligonucleotides and subcloned between the EcoRI and BamHI sites of pGBT9 expression vector. The orientation and sequence was verified by DNA sequence analysis. The yeast strain HF7c was then sequentially transformed with the prepared MAP17-pGBT9 vector; and then used as a bait with a normal human kidney cDNA library in the pGAD10 expression vector (Clontech, Palo Alto, Calif.) after one round of amplification. Potentially interacting clones were selected on synthetic dropout (SD) medium containing all amino acids except Trp, Leu, and His, in the presence of 5 mM 3-amino-1,2,4-triazole (3-AT). Yeast colonies expressing potential interacting proteins were further tested using an X-Gal reporter assay (Sigma Inc.; St. Louis, Mo.) according to the manufacturer's protocol. The activating domain plasmids corresponding to each positive clone were rescued on selection media lacking Leucine after transformation of *E. Coli* HB101. Plasmid DNA from each clone was purified using standard techniques [Sambrook et al., *Molecular Cloning: A Laboratory Manual*, Cold Spring Harbor Laboratory Press, 1989]; and subjected to DNA sequencing using oligonucleotide primers (Integrated DNA Technologies, Coralville, Iowa) and a 373 automated DNA sequencer from Applied Biosystems (Branchburg, N.J.). The Genebank was also searched for sequence homologies using the Hyperblast program.

In-Vitro Translation

An XhoI-BglI DNA fragment corresponding to the largest cDNA clone was subcloned between the XhoI and BamHI sites of pGEM7Zf (Promega, Madison, Wis.) and submitted to in-vitro translation using the reticulocyte lysate system from Promega according to the manufacturer's protocol in the presence of 35S-methionine (Amersham, Arlington Heights, Ill.). Translated RNA products were analyzed on SDS-PAGE and detected by autoradiography.

Fusion Protein Production

For fusion protein production, a BgIII DNA fragment containing the complete PDZK1 cDNA clone was subcloned into the BamHI site of the glutathione-S-transferase (GST)-fusion vector pGEX-3X (Amrad Corporation Ltd., Melbourne, Australia). *E. Coli* JM109 cells were transformed with the prepared recombinant plasmids. Fusion protein production was induced with 0.5 mmol/l isopropyl-β-D-thiogalactopyranoside (IPTG). The fusion proteins (GST and GST-PDZK1) were then affinity purified using a glutathione-sepharose column (Pharmacia, Uppsala, Sweden) as previously described [Smith, D. B. and K. S. Johnson, *Gene* 67: 31–40 (1988); Kocher et al., *Am. J. Pathol.* 137: 1509–1524 (1990)].

Specific Antibody Against PDZK1 Protein

A polyclonal antibody against PDZK1 was prepared against the GST-PDZK1 fusion protein. Chicken were immunized and IgY were recovered from egg yolks. Anti-PDZK1 antibodies were subsequently purified by affinity chromatography using a GST-PDZK1 affinity column after absorption of IgY against GST-Sepharose.

Western Blot Analysis of Proteins

For Western blot analysis, protein extracts were electrophoresed on SDS-PAGE; transferred to nitrocellulose; and then incubated with the anti-PDZK1 antibody, or chicken IgY as a control, at a concentration of 3 µg/ml. The Western blot was subsequently incubated with a biotinylated anti-chicken IgG at 1/500; and then incubated with Avidin-horse radish peroxidase at 1/10,0000 (Sigma, St. Louis, Mo.). These incubations were followed by a diaminobenzidine reaction (Sigma).

Immunoperoxidase Studies

Tissues were collected in the operating room; fixed for 4 hours in 4% paraformaldehyde in phosphate-buffered saline, pH 7.4, at 4° C.; and then transferred to 30% sucrose in phosphate-buffered saline (pH 7.4) overnight at 4° C. Tissues were then frozen in OCT compound (Miles Diagnostics, Elkhart, Ind.) and stored in liquid nitrogen. Immunoperoxidase studies were performed on 6 µm fixed-frozen tissue sections using either the affinity-purified primary antibody against PDZK1 or chicken IgY as a control at a concentration of 5 µg/ml. The prepared tissue sections were then incubated with a biotinylated anti-chicken IgG using a 1/200 dilution (Vector, Burlingame, Calif.); and subsequently treated with the Vectastain ABC reagents (Vector) and diaminobenzidine (Research Genetics, Inc., Huntsville, Ala.), according to the manufacturer's protocol.

Determination Of The Homophilic Interaction Of PDZK1 To MAP17

In order to confirm the interaction of MAP17 and PDZK1, a normal kidney total protein extract was run on an SDS-PAGE medium with appropriate size markers; and then transferred to nitrocellulose membrane in 25 mM Tris, 192 mM glycine, and 20% methanol, pH 8.3. The prepared nitrocellulose membrane was sequentially incubated for six hours at 37° C. with either the fusion protein GST-PDZK1 or GST alone in PBS buffer at a concentration of 50 µg/ml; followed by an overnight incubation at 4° C. with an anti-*Schistosoma japonicum* GST polyclonal antibody at a dilution of 1/500 (Santa Cruz Biotechnology, Santa Cruz, Calif.). Filters were then incubated with an anti-rabbit IgG conjugated to horseradish peroxidase at a dilution of 1/500 (GIBCO-BRL, Gaithesburg, Md.). The binding was detected on the filters using ECL chemiluminescent substrate (Pierce, Rockford, Ill.).

Mammalian Two-Hybrid Assay

In order to demonstrate that MAP17 and PDZK1 interact within mammalian cells, a mammalian two-hybrid assay was used (Clontech). The cytoplasmic hydrophilic region of MAP17 (used for the yeast two-hybrid screening) was subcloned between the EcoRI and BamHI sites of the pM expression vector and a BgIII-DNA fragment containing the complete PDZK1 coding sequence was subcloned into the BamHI site of pVP16. Cultured HT1080 fibrosarcoma cells (ATCC, Rockville, Md.) were transfected in the presence of calcium phosphate with 2 µg pG5CAT reporter plasmic and 4 μg of each of either the two recombinant plasmids (pH-MAP17/pVP16-pDzK1) or control plasmids (pM-53/pVP16-CP), as previously described [Ausubel, F. M., *Current Protocols In Molecular Biology*, Vols. 1 and 2, Wiley & Sons, Inc., 1989; Claffey et al., *J. Biol. Chem.* 267: 16317–16322 (1992)]. Transfected cells were allowed to grow for 48–72 hours. CAT activity was measured using a CAT enzyme assay system (from Promega) according to the manufacturer's protocol in the presence of $^{14}$C-chloramphenicol (New England Nuclear, Boston, Mass.).

Northern and In-Situ Hybridization Studies

Normal human tissue Northern blots were purchased from Clontech. Northern blots were hybridized with the PDZK1 cDNA probe isolated from a human kidney library labeled with $^{32}$p-dCTP (New England Nuclear) using a random primer labeling kit from Amersham as previously described [Kocher et al., *Clin. Cancer Res.* 1: 1209–1215 (1995)].

In-situ hybridization was performed on 6 μM fixed-frozen tissue sections using single-stranded antisense or control sense 35S-labeled riboprobes as previously described [Brown et al., *Cancer Res.* 53: 4727–4735 (1993)]. Sense and anti-sense cRNA probes were generated after ligating an XhoI-BgIII one kb DNA fragment corresponding to the 5'-end of the PDZK1 cDNA clone into pGEM7Zf and linearization with StyI.

B. Empirical Data and Results

Experimental Series 1: Isolation of PDZK1 Using the Yeast Two Hybrid System

A 200 bp DNA fragment corresponding to the intracytoplasmic domain of MAP17 was generated by PCR (Polymer Chain Reaction) using sequence specific oligonucleotide primers and subcloned between the EcoRI and BamHI sites of pGBT9. The recombinant plasmid was used as a bait to screen a normal kidney cDNA library prepared in the pGAD10 vector. Yeast colonies were grown on selection media lacking typtophan leucine and histidine in order to allow growth of yeast successfully transformed with vectors encoding two interacting proteins. Such yeast colonies were subsequently tested for GAL4 activation using the X-Gal reporter assay. Using this technique, seven cDNA clones potentially encoding for proteins interacting with the intracytoplasmic domain of MAP17 were selected for further study and submitted for DNA sequencing. Sequence analysis revealed that three of the seven cDNA clones corresponded to the same gene. Two of them were 2.1 kb long and the third one was 1.0 kb long and corresponded to the 5'-end of the others.

The longest clone was sequenced entirely to reveal that it encodes a protein of 519 amino acids. This is illustrated by FIG. 3. To verify that the longest cDNA clone contained the complete coding sequence of the protein, the corresponding DNA fragment was subcloned into pGEM7Zf and submitted to a cell-free in-vitro translation using a reticulocyte lysate system. The autoradiography results of an SDS-PAGE analysis revealed a single band at 63 kD, consistent with the predicted molecular weight from the cDNA sequence. This result is shown by FIG. 4.

A search of the Genebank revealed that the amino acid sequence submitted did not share complete homology with any known protein and therefore was a newly identified gene product. However, it shared significant homologies with a number of proteins containing PDZ-protein interaction domains. Accordingly, the novel protein and gene was named PDZK1. PDZK1 protein contains four PDZ domains which are between 54 and 80 amino acids long sharing up to 45% identity with other PDZ-domain containing proteins (see FIG. 3). The sequence of the PDZK1 cDNA clone was submitted to the Genebank, where it has received the accession number AF012281.

Experimental Series 2: Determination of the Homophilic Interaction of PDZK1 Protein with MAP17 Protein In-Vitro.

Figure 5:
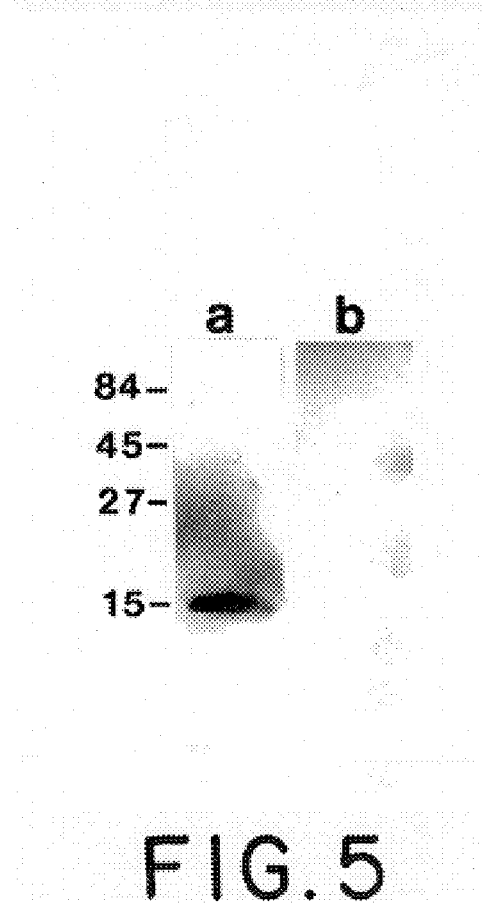
FIG. 5 is a photograph illustrating a human kidney protein extract on SDS-PAGE medium, transferred to nitrocellulose, and incubated with either (a) GST-PDZK1 fusion protein or (b) GST alone.

In order to demonstrate that PDZK1 interacts with MAP17 in-vitro, the experiments evaluated the binding of PDZK1-glutathione-S-transferase (PDZK1-GST) fusion protein and glutathione-S-transferase (GST) to a normal human kidney protein extract. The kidney protein extract was analyzed on SDS-PAGE media; subsequently transferred to a nitrocellulose membrane; and then combined with (a) PDZK1-GST or (b) GST alone. Using this technique, a single band between 15 and 17 kD was visualized corresponding to the molecular weight of MAP17, column (a), as shown in FIG. 5. This showed that the two proteins interact in-vitro. In comparison, incubation of the Western blot with GST alone did not show any binding activity as evidenced by FIG. 5, column (b).

Figure 6:
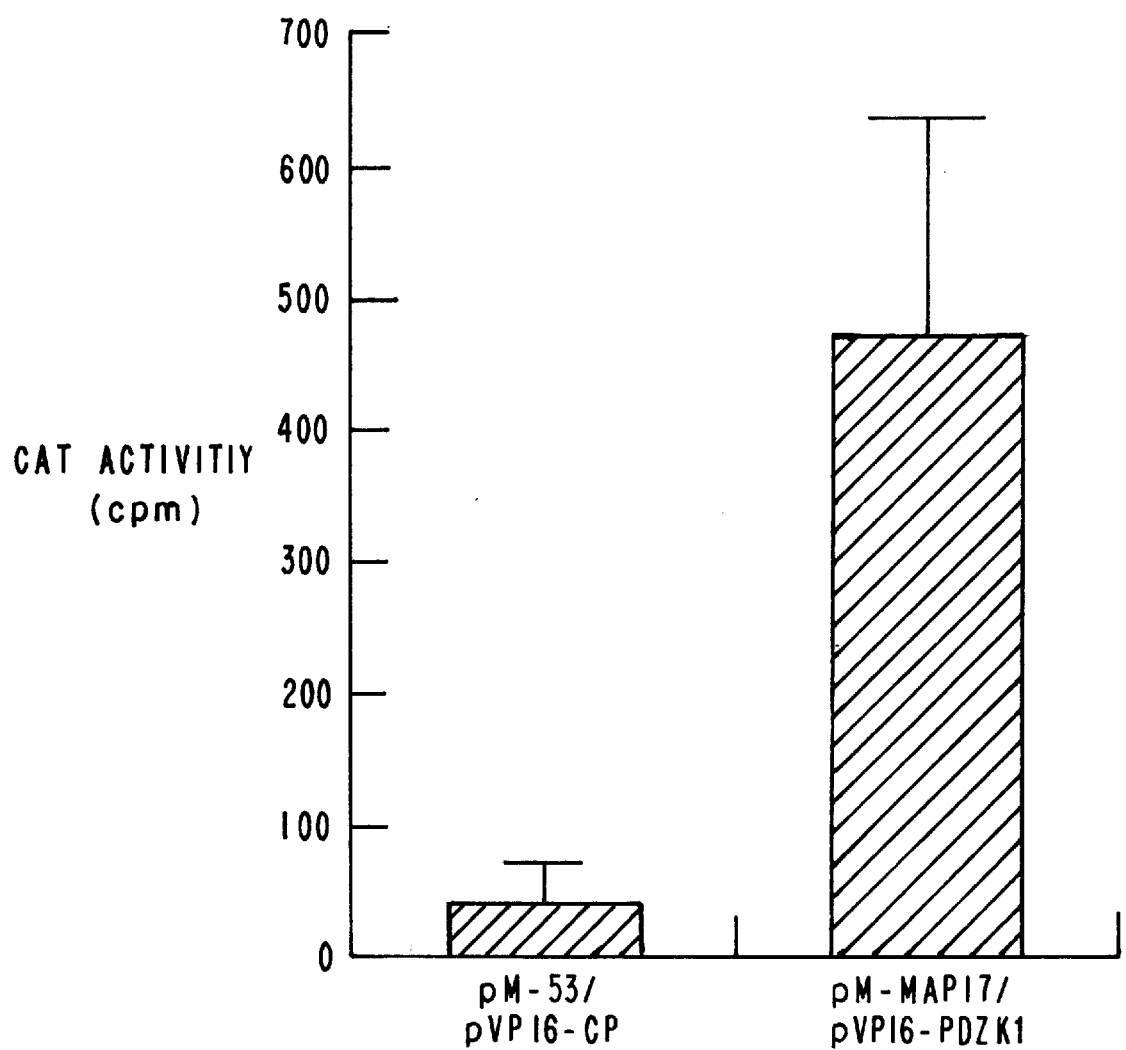
FIG. 6 is a graph illustrating the in-vivo interaction of MAP17 with PDZK1 protein evaluated using the mammalian two hybrid assay after transfection of HT 1080 fibrosarcoma cells.

Experimental Series 3: Determination of the Interaction of PDZK1 Protein and MAP 17 Protein in Mammalian Cells In order to demonstrate that MAP17 and PDZK1 interact in mammalian cells, a mammalian two-hybrid assay was used (Clontech). In this in-vivo system, interacting proteins activate the chloramphenicol acetyltansferase (CAT) reporter gene. CAT activity measured following transfection of HT1080 fibrosarcoma cells with pM-MAP17 and pVP16-PDZK1 plasmids was significantly increased compared to transfection of negative control plasmids pM-53 and pVP16-CP (p<0.005). This data and result is shown by FIG. 6. These data evidence and confirm the in-vivo interaction of MAP17 and PDZK1 in cultured mammalian cells.

Figure 7:
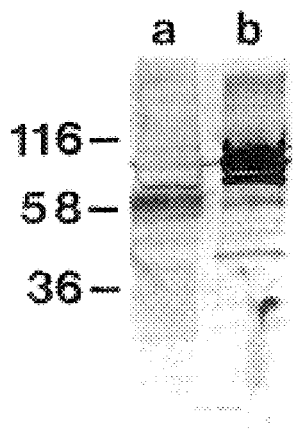
FIG. 7 is a photograph illustrating Western blot analysis of a reduced human kidney protein extract and the GST PDZK1 fusion protein incubated with affinity purified antibody specific against PDZK1 protein.

Experimental Series 4: Generation of a Specific Antibody Against PDZK1 and Localization of PDZK1 in Human Adult Kidney A GST-PDZK1 fusion protein (prepared as described previously herein) was used as an antigen to produce a chicken polyclonal antibody. The specific anti-PDZK1 antibody was purified from egg yolk by affinity chromatography using a GST-PDZK1 affinity column after absorption of chicken IgY against GST-sepharose. A Western blot analysis showed that the PDZK1 antibody specifically reacted with the isolated 60 kD band consistent with (a) PDZK1 in a human kidney protein extract, as well as with (b) GST-PDZK1 fusion protein. This is illustrated by FIG. 7, columns (a) and (b) respectively.

Figure 8:
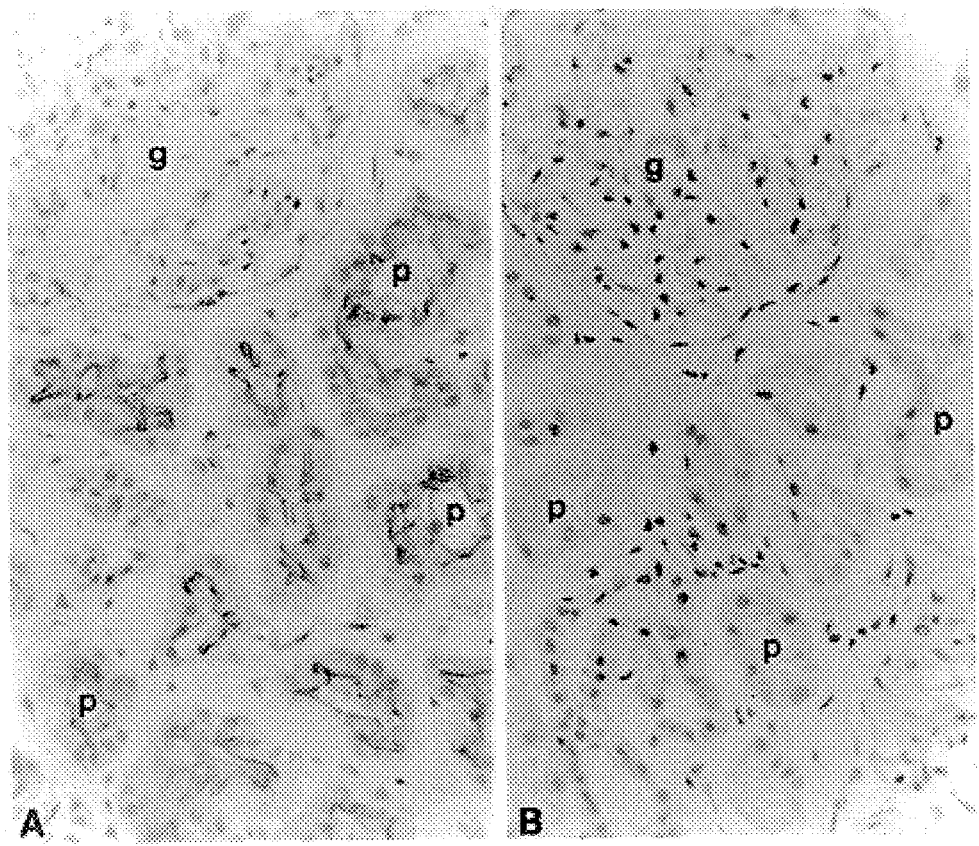
FIGS. 8A and 8B are photographs of immunoperoxidase staining of normal human renal cortex with anti-PDZK1 antibody or normal chicken IgY.

Immunoperoxidase studies conducted subsequently demonstrated that the PDZK1 antibody selectively labeled the brush border of renal proximal tubular epithelial cells in a pattern identical to that of MAP17. Normal human renal cortex was combined with anti-PDZK1 antibody or with normal chicken IgY as a negative control. This results are shown by FIGS. 8A and 8B. FIG. 8A is a X300 photograph and shows the positive staining of human renal cortex using the anti-PDZK1 antibody which is limited to the brush border of proximal tubular epithelial cells (P) while the glomerul (g) are not labeled. In comparison, while FIG. 8B shows a negative result using normal chicken IgY.

Figure 9:
FIG. 9 is a photograph of Northern blot hybridizations of RNA individually extracted from (a) human heart, (b) brain, (c) placenta, (d) lung, (d) liver, (f) skeletal muscle, (g) kidney, (h) pancreas, (i) adrenal medulla, (j) thyroid, (k) adrenal cortex, (l) testis, (m) thymus, (n) small intestine and (o) stomach.

Experimental Series 5: Characterization of PDZK1 by Northern Blot and In-Situ Hybridization Northern blots hybridization with the PDZK1 cDNA probe (prepared as previously described herein) detected an mRNA transcript of 2.4 kb. This mRNA transcript was found expressed in some normal tissues—such as normal kidney, pancreas, liver and small intestine; and at lower concentration levels in adrenal cortex, testis, and stomach. However, PDZK1 was not detectable in other normal tissues and organs—notably normal heart, brain, placenta, lung, adrenal medulla, thyroid, and thymus. These data and results are shown by FIG. 9.

In order to determine the cellular localization of PDZK1, in-situ hybridization studies were performed. Using an antisense RNA probe derived from the PDZK1 cDNA clone, an evaluation of a number of tissue samples was made—first from normal adult human kidney, breast, lung and gastrointestinal tract; and then subsequently as carcinomas arising from the same organs. These results are shown by FIGS. 10A–10L.

Figure 10:
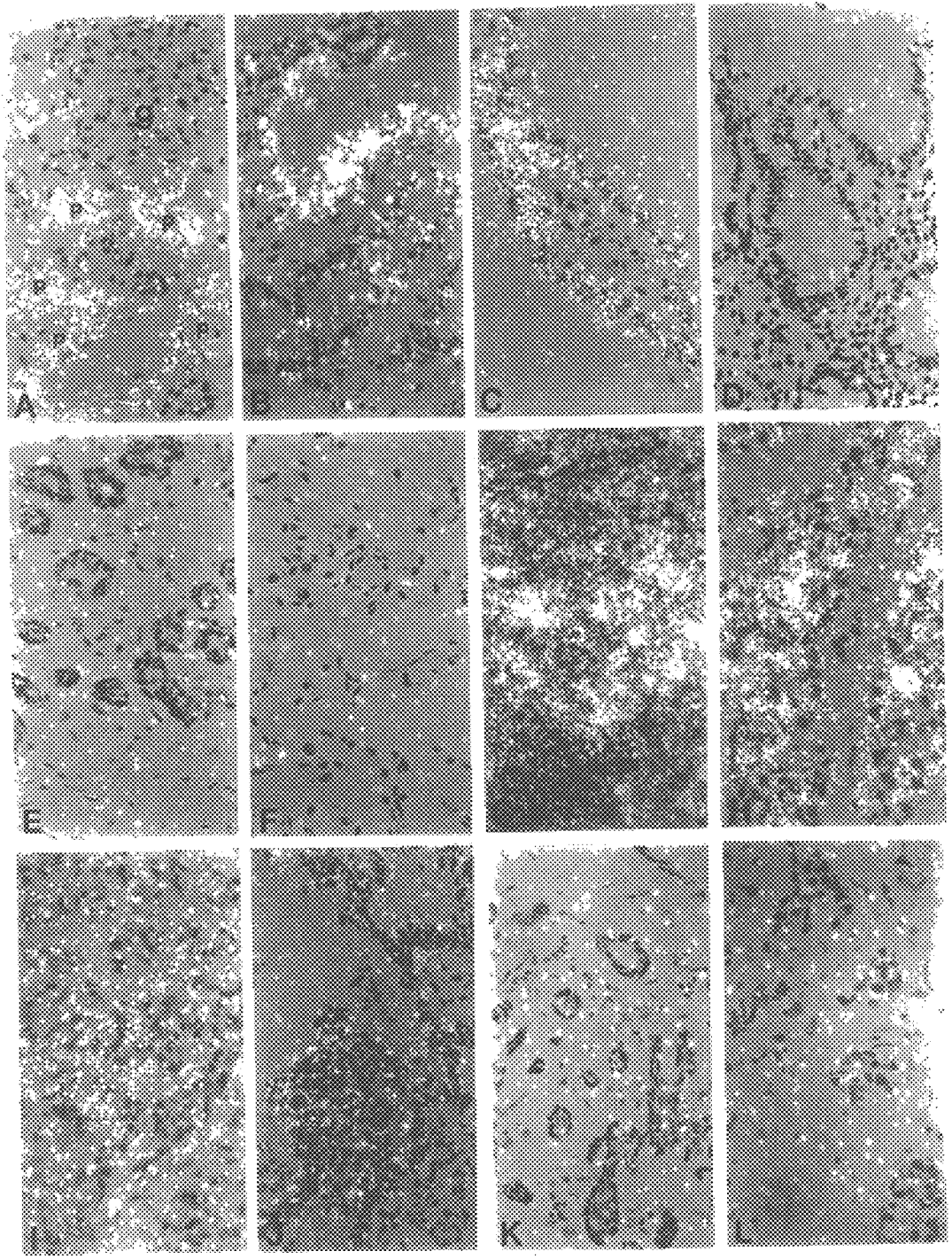
FIGS. 10A–10L are X200 photographs illustrating in-situ hybridization via silver grains using a PDZK1 cRNA probe with a variety of different human normal and neoplastic tissues.

Note that in the normal kidney, PDZK1 protein is highly expressed in proximal tubular epithelial cells, in a pattern identical to that produced by MAP17. However, PDZK1 is either not expressed at all or expressed at very low quantitative levels in the remainder of the normal renal parenchyma as shown by FIG. 10A. PDZK1 protein is also expressed in glandular epithelial cells of stomach and small bowel as shown by FIGS. 10B–10C respectively. Nevertheless, PDZK1 protein is not detectable in colonic mucosa as shown by FIG. 10D. Finally, normal breast and normal lung tissue samples showed either no or minimal background labeling for PDZK1 as shown by FIGS. 10E–10F respectively.

In comparison, renal cell carcinomas showed a diffuse expression of PDZK1 in 3 out of 4 cases studied (75%). PDZK1 protein was expressed by virtually all malignant cells with varying degrees of high intensity as shown by FIG. 10G. In addition, PDZK1 protein is overexpressed in 5 out of nine cases (55%) of infiltrating carcinomas of the breast; in 1 out of 4 cases (25%) of colonic carcinomas; and in 1 out of 4 lung carcinomas studied (25%) compared to normal tissue samples. These results are shown by FIGS. 10H–10J respectively. Finally, control hybridization experiments using a sense cRNA probe showed only minimal background labeling in tissue sections of normal breast and carcinoma of the breast as shown by FIGS. 10K and 10L respectively.

In all cases empirically studied, PDZK1 expression was confined to cells of epithelial origin; mesenchymal and inflammatory cells were not detectably labeled in this assay, indicating that PDZK1 protein was not expressed within these cell types. Control hybridization using a sense cRNA probe were invariably negative on all mesenchymal and inflammatory cell tissue studied, whether benign or malignant.

The present invention is not to be restricted in form nor limited in scope except by the claims appended hereto.

What I claim is:

1. A human PDZK1 protein whose presence indicates an ongoing neoplastic development within cells and tissues of epithelial cell origin, said PDZK1 protein comprising
 a polypeptide
  (i) having a molecular weight of about 63 kD as defined by SDS polyacrylamide gel electrophoresis;
  (ii) which is comprised of about 519 amino acids;
  (iii) having four distinct PDZ domains as part of its overall structure, each of said PDZ domains varying in size from 54–80 amino acids;
  (iv) which is devoid of a SH3 binding domain;
  (v) which does not contain a guanylate kinase domain; and
  (vi) which interacts with the membrane associated protein MAP17.

2. A human PDZK1 protein whose presence indicates an ongoing neoplastic development within cells and tissues of epithelial cell origin, said PDZK1 protein comprising the amino acid sequence as recited by FIG. 2 (SEQ ID NO:2).

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2040 base pairs
      (B) TYPE: nucleic acid
      (C) STRANDEDNESS: single
      (D) TOPOLOGY: linear (xi) SEQUENCE DESCRIPTION: SEQ ID NO:1:

```
GAA TTC CGG GCA GCT CCT CTT CCA TCT CCA GAA ATG ACC TCC ACC TTC        48

AAC CCC CGA GAA TGT AAA CTG TCC AAG CAA GAA GGG CAA AAC TAT GGC        96

TTC TTC CTG CGA ATT GAG AAG GAC ACC GAG GGC CAC CTG GTC CGG GTG       144

GTT GAG AAG TGT AGC CCA GCA GAG AAG GCT GGC CTT CAA GAT GGA GAC       192

AGA GTT CTT AGG ATC AAT GGT GTC TTT GTG GAC AAA GAA GAA CAT ATG       240

CAG GTT GTG GAT CTG GTC AGA AAG AGT GGG AAT TCA GTG ACT TTA CTA       288

GTT CTG GAT GGG GAT TCC TAT GAG AAA GCA GTG AAA ACA CGG GTG GAC       336

TTG AAA GAG TTG GGT CAA AGT CAG AAG GAG CAA GGT TTG AGT GAT AAT       384

ATA CTT TCC CCT GTG ATG AAT GGA GGT GTG CAA ACT TGG ACC CAG CCC       432

CGG CTC TGC TAT CTC GTG AAG GAA GGA GGC AGC TAT GGC TTC TCT CTG       480

AAA ACT GTC CAA GGT AAA AAG GGG GTG TAC ATG ACT GAT ATT ACA CCT       528

CAA GGT GTG GCT ATG AGA GCT GGA GTT CTG GCT GAT GAT CAC TTG ATT       576

GAA GTG AAT GGA GAG AAT GTA GAG GAT GCC AGC CAT GAG AAA GTG GTT       624
```

-continued

```
GAA AAG GTG AAG AAG TCA GGA AGC CGT GTC ATG TTC CTG CTG GTG GAC      672

AAA GAA ACT GAC AAG CGT CAT GTT GAG CAG AAG ATA CAA TTC AAA AGA      720

GAA ACA GCC AGT TTG AAA CTG TTA CCC CAC CAG CCC CGA ATT GTG GAG      768

ATG AAG AAA GGA AGC AAT GGC TAT GGT TTC TAT CTG AGG GCA GGC TCA      816

GAA CAG AAA GGT CAA ATC ATC AAG GAC ATA GAT TCT GGA AGT CCA GCA      864

GAG GAG GCT GGC TTG AAG AAC AAT GAT CTG GTA GTT GCT GTC AAC GGC      912

GAG TCT GTG GAA ACC CTG GAT CAT GAC AGT GTG GTA GAA ATG ATT AGA      960

AAG GGT GGA GAT CAG ACT CAC TTG GTG CTA GAC AAA GAG ACG GAC         1008

AAC ATG TAC AGA CTG GCT CAT TTT TCT CCA TTT CTC TAC TAT CAA AGT     1056

CAA GAA CTG CCC AAT GGC TCT GTC AAG GAG GCT CCA GCT CCT ACT CCC     1104

ACT TCT CTG GAA GTC TCA AGT CCA CCA GAT ACT ACA GAG GAA GTA GAT     1152

CAT AAG CCT AAA CTC TGC AGG CTG GCT AAA GGT GAA AAT GGC TAT GGC     1200

TTT CAC TTA AAT GCG ATT CGG GGT CTG CCA GGC TCA TTC ATC AAA GAG     1248

GTA CAG AAG GGC GGT CCT GCT GAC TTG GCT GGG CTA GAG GAT GAG GAT     1296

GTC ATC ATT GAA GTG AAT GGG GTG AAT GTG CTA GAT GAA CCC TAT GAG     1344

AAG GTG GTG GAT AGA ATC CAG AGC AGT GGG AAG AAT GTC ACA CTT CTA     1392

GTC TGT GGA AAG AAG GCC TAT GAT TAT TTC CAA GCT AAG AAA ATC CCT     1440

ATT GTT TCC TCC CTG GCT GAT CCA CTT GAC ACC CCT CCA GAT TCT AAA     1488

GAA GGA ATA GTG GTG GAG TCA AAC CAT GAC TCG CAC ATG GCA AAA GAA     1536

CGG GCC CAC AGT ACA GCC TCA CAT TCT TCT TCC AAT TCT GAA GAT ACA     1584

GAG ATG TGA TGA AAA CAA GTA ATA GCT TTG GCT GTT TAT TTG ATA GCT     1632

GTT TCT GGG TAT TTA ATA GGA ATC CTT TCT CAA GGA ATG AGT TGT GAC     1680

CTG TTT ACT GTC TCT TTA GAA GAA AAA CTC CAC TGG AAA CCA TTC ACC     1728

ATG TGT GAC TGT CTT CTG TTA TCA TTT GTC TTA CAG GCG GCT ATT GCA     1776

GAC GGC TAA TTT ATG CTT AAC TTA GGA AGA GAT AAG GCA AGA GCT AGA     1824

TTT TTT TCA TGT GAT CTT TTC CAA GCT TCA ACT TAA CTT AAC TAC ATT     1872

TCT CTG TAT GAT GAT GTC TCT TAC TTC TAC AGG TTC CTT GAG CAC CAA     1920

AGA TGA TTC ATA ACT CTG TAT AGG TGA CAG CTG CTT ATA AAA GCA TCT     1968

TAG CAG ATA AGC CTA TTA AAA TTG TGC TTT TGT AAC AAT GTT GTG GTT     2016

GCT AGA ATA AAT ACC ATG AAC CCG                                     2040
```

(2) INFORMATION FOR SEQ ID NO:2:

(i) SEQUENCE CHARACTERISTICS:
        (A) LENGTH: 519 amino acids
        (B) TYPE: amino acid
        (C) STRANDEDNESS: single
        (D) TOPOLOGY: linear (xi) SEQUENCE DESCRIPTION: SEQ ID NO:2:

```
Met Thr Ser Thr Phe Asn Pro Arg Glu Cys Lys Leu Ser Lys Gln Glu
 1               5                  10                  15

Gly Gln Asn Tyr Gly Phe Phe Leu Arg Ile Glu Lys Asp Thr Glu Gly
            20                  25                  30

His Leu Val Arg Val Val Glu Lys Cys Ser Pro Ala Glu Lys Ala Gly
        35                  40                  45
```

-continued

```
Leu Gln Asp Gly Asp Arg Val Leu Arg Ile Asn Gly Val Phe Val Asp
     50                  55                  60
Lys Glu Glu His Met Gln Val Val Asp Leu Val Arg Lys Ser Gly Asn
 65                  70                  75                  80
Ser Val Thr Leu Leu Val Leu Asp Gly Asp Ser Tyr Glu Lys Ala Val
                 85                  90                  95
Lys Thr Arg Val Asp Leu Lys Glu Leu Gly Gln Ser Gln Lys Glu Gln
             100                 105                 110
Gly Leu Ser Asp Asn Ile Leu Ser Pro Val Met Asn Gly Gly Val Gln
             115                 120                 125
Thr Trp Thr Gln Pro Arg Leu Cys Tyr Leu Val Lys Glu Gly Gly Ser
    130                 135                 140
Tyr Gly Phe Ser Leu Lys Thr Val Gln Gly Lys Lys Gly Val Tyr Met
145                 150                 155                 160
Thr Asp Ile Thr Pro Gln Gly Val Ala Met Arg Ala Gly Val Leu Ala
                165                 170                 175
Asp Asp His Leu Ile Glu Val Asn Gly Glu Asn Val Glu Asp Ala Ser
            180                 185                 190
His Glu Lys Val Val Glu Lys Val Lys Ser Gly Ser Arg Val Met
            195                 200                 205
Phe Leu Leu Val Asp Lys Glu Thr Asp Lys Arg His Val Glu Gln Lys
    210                 215                 220
Ile Gln Phe Lys Arg Glu Thr Ala Ser Leu Lys Leu Leu Pro His Gln
225                 230                 235                 240
Pro Arg Ile Val Glu Met Lys Lys Gly Ser Asn Gly Tyr Gly Phe Tyr
                245                 250                 255
Leu Arg Ala Gly Ser Glu Gln Lys Gly Gln Ile Ile Lys Asp Ile Asp
            260                 265                 270
Ser Gly Ser Pro Ala Glu Glu Ala Gly Leu Lys Asn Asn Asp Leu Val
        275                 280                 285
Val Ala Val Asn Gly Glu Ser Val Glu Thr Leu Asp His Asp Ser Val
    290                 295                 300
Val Glu Met Ile Arg Lys Gly Gly Asp Gln Thr Ser Leu Leu Val Val
305                 310                 315                 320
Asp Lys Glu Thr Asp Asn Met Tyr Leu Arg Ala His Phe Ser Pro Phe
                325                 330                 335
Leu Tyr Tyr Gln Ser Gln Glu Leu Pro Asn Gly Ser Val Lys Glu Ala
            340                 345                 350
Pro Ala Pro Thr Pro Thr Ser Leu Glu Val Ser Ser Pro Pro Asp Thr
        355                 360                 365
Thr Glu Glu Val Asp His Lys Pro Lys Leu Cys Arg Leu Ala Lys Gly
    370                 375                 380
Glu Asn Gly Tyr Gly Phe His Leu Asn Ala Ile Arg Gly Leu Pro Gly
385                 390                 395                 400
Ser Phe Ile Lys Glu Val Gln Lys Gly Gly Pro Ala Asp Leu Ala Gly
                405                 410                 415
Leu Glu Asp Glu Asp Val Ile Ile Glu Val Asn Gly Val Asn Val Leu
            420                 425                 430
Asp Glu Pro Tyr Glu Lys Val Val Asp Arg Ile Gln Ser Ser Gly Lys
        435                 440                 445
Asn Val Thr Leu Leu Val Cys Gly Lys Lys Ala Tyr Asp Tyr Phe Gln
    450                 455                 460
```

-continued

```
Ala Lys Lys Ile Pro Ile Val Ser Ser Leu Ala Asp Pro Leu Asp Thr
465             470                 475                 480

Pro Pro Asp Ser Lys Glu Gly Ile Val Val Glu Ser Asn His Asp Ser
                485                 490                 495

His Met Ala Lys Glu Arg Ala His Ser Thr Ala Ser His Ser Ser Ser
                500                 505                 510

Asn Ser Glu Asp Thr Glu Met
            515
```